United States Patent [19]

Seyl

[11] 3,947,329
[45] Mar. 30, 1976

[54] METHOD OF MEASURING ACCELERATED CORROSION RATE

[76] Inventor: Robert G. Seyl, 1123 Mulford St., Evanston, Ill. 60202

[22] Filed: Dec. 9, 1974

[21] Appl. No.: 530,870

[52] U.S. Cl.............................. 324/29; 204/195 C
[51] Int. Cl.² ................. G01N 27/46; G01N 27/26
[58] Field of Search............. 204/19, 195 C; 324/29, 324/71 R

[56] References Cited
UNITED STATES PATENTS

| 3,694,324 | 9/1972 | Seyl | 204/1 T |
| 3,850,736 | 11/1974 | Seyl | 204/195 C |

*Primary Examiner*—T. Tung
*Assistant Examiner*—Aaron Weisstuch
*Attorney, Agent, or Firm*—Mann, Brown & McWilliams

[57] ABSTRACT

An improvement in the measurement of accelerated corrosion rate when measured on two duplicated electrodes in accordance with U.S. Pat. No. 3,694,324. Difference in free electrode potential between said electrodes is first determined. A means is introduced for varying the ohmic resistance ratio of the isolation resistors through which the cathodic polarizing current is passed to said electrodes. The cathodic current is then applied at a selected rate of increase from zero while said ratio is adjusted to maintain said difference in potential. The cathodic current is then removed and said electrodes are allowed to return to said difference in potential. Measurement is then continuously made of the relationship between corrosion current measured on said electrodes and said cathodic current increased in said manner.

11 Claims, 8 Drawing Figures

METHOD OF MEASURING ACCELERATED CORROSION RATE

This invention relates to device and method for measuring the accelerated corrosion of electronic conductors by non-gaseous ionic conductors, and more specifically is directed to a device and method for cathodically polarizing duplicated electrodes in such measurement.

This application is related to my U.S. Pat. No. 3,850,736 issued Nov. 26, 1974, filed Sept. 25, 1972, which is a division of my U.S. Pat. No. 3,694,324, issued Sept. 26, 1972 and filed January 16, 1969.

BACKGROUND OF THE INVENTION

In the measurement of accelerated corrosion rate as disclosed in my U.S. Pat. No. 3,694,324, the corrosion current $i_A$ occurring at the free electrode potential is measured first.

This measurement of current $i_A$, when made according to my U.S. Pat. No. 3,250,689, employs a corrosion cell containing the ionically conducting corrosive into which are immersed a measured electrode, a reference electrode for measuring its potential, and an opposed electrode for passing DC current to or from the measured electrode. A DC voltage is applied to the measured and opposed electrodes to polarize the measured electrode within the substantially linear relationship range between polarizing DC current and resulting polarization voltage that extends from slightly above zero to about 0.03 volt of polarization in either anodic or cathodic direction, and measurement is made of the polarizing current $i_p$ and of the resulting polarization voltage $e_p$ after the current-potential relationship first approaches a selected slow rate of change. Then, according to my U.S. Pat. No. 3,156,631, the measured current $i_p$ is converted to the corrosion current $i_A$ through linear proportionality with the Direct Voltage $E_d = 0.028$ to $0.030$ volt, as $i_A = i_p(\frac{1}{2}E_d/e_p)$. The polarization voltage $e_p$ may be produced in cathodic direction in the form of $e_{pc}$, or in the anodic direction in the form of $e_{pa}$, and the corrosion current $i_A$ can be measured from the average of these two measurements.

When current $i_A$ is measured according to my U.S. Pat. No. 3,069,332, only two measured electrodes are required, usually in the form of duplicated electrodes. The polarizing DC voltage is applied to these electrodes to produce the polarizing current $i_p$ which polarizes the one electrode cathodically by the voltage $e_{pc}$ and the other electrode anodically by the voltage $e_{pa}$. When the ionic conductor resistance is negligible, the DC voltage applied to the electrodes measures the sum of $e_{pc}$ and $e_{pa}$, and $i_A = (i_p)(E_d)/(e_{pa}+e_{pc}) = (i_p)(E_d)/$(applied DC Voltage). A second measurement of $i_A$ can be made with reversed polarity of the applied DC voltage, to average the two measurements.

Following this measurement of current $i_A$, the presence or absence of accelerated corrosion is detected by applying an increment of cathodic polarizing current $i_x$ to the measured electrode, or to each of duplicated measured electrodes, through a means not interfering with corrosion current measurement, while measuring polarizing current $i_p$. If current increment $i_x$ produces an increase in current $i_p$, there is no evidence of accelerated corrosion mechanism operation, and the rate-determining corrosion current $i_R$ is determined as, $i_R = i_A$, where $i_R$ can be applied directly through Faraday's Law of Electrolysis to convert current into rate of metal weight loss.

If current increment $i_x$ produces a decrease in current $i_p$, the presence of accelerated corrosion mechanism is indicated. Measurement is then made of change in value of current $i_p$ produced by increase in value of current $i_x$, to determine the minimum value of current $i_p$, termed $i_{pb}$, produced by the application of current $i_x$. Current $i_{pb}$ is converted to bounding corrosion current $i_B$ through the Direct Voltage $E_d$, as described above. The accelerated corrosion mechanism then measures corrosion rate as, $i_R = 2.4(i_A) - i_B$. Alternatively, but generally with less accuracy, the current $i_{xb}$ at which $i_{pb}$ occurs, can be measured and taken as $i_R = i_{xb}$.

One alternative means for cathodically polarizing the measured electrode by current $i_x$ while not interfering with the corrosion current measurement, is through what is termed a circuit isolation device, operated as follows. When current $i_A$ is measured with two electrodes, they are taken in the form of duplicated measured electrodes. When current $i_A$ is measured with one measured electrode, a reference electrode and an opposed electrode, the reference electrode is taken in the form of a duplication of the measured electrode. The positive pole of a source of variable DC voltage is connected to an additional electrode operated as an anode. The negative pole is connected to two isolation resistors of equal ohmic value. Each of the two duplicated electrodes is connected to the negative pole through one of the isolation resistors. The ohmic value of the isolation resistors is selected to be large enough to cause an acceptable small current to flow through them from DC voltage subsequently applied or produced between the duplicated electrodes during $i_p$ measurement. This current through the isolation resistors may be taken as a maximum value of about 10 % of measured corrosion current $i_A$. A meter in series with said source of variable DC voltage measures the total cathodic polarizing current $2i_x$.

Said U.S. Pat. No. 3,694,324 describes two alternative methods for operating the circuit isolation device. In one alternative, the relationship between cathodic polarizing current $i_x$ and polarizing current $i_p$ of corrosion current measurement is measured from a series of points of relationship measurement made at selected increments of $i_x$. In the other alternative, the relationship is continuously measured as current $i_x$ is applied at a selected rate of increase. The measurement of the current $i_x$ and $i_p$ relationship from pointwise measurement has one advantage. The increment of current $i_x$ is applied first, and if a difference in potential is produced between the duplicated electrodes, it can be equalized before application of the DC voltage to produce the current $i_p$ measurement. Its disadvantages include the requirement for a plurality of repeated method operation steps which consume time and are not readily automated.

In theory, measurement of the current $i_x$ and $i_p$ relationship through continuous application of current $i_x$ at a selected rate of increase minimizes the time required for measurement of current $i_{pb}$ or $i_{xb}$, and is more easily automated. In practice, such continuous measurement if found to be unreliable even under the most favorable conditions of laboratory precision in using duplicated electrodes of equal area and isolation resistors of equal ohmic value. Its reliability is further decreased when the anode electrode of the circuit isolation device is brought to close equidistant spacing from the duplicated electrodes, as is required for a corrosion probe of reasonably small diameter. To illustrate this, in some instances initial increase of $i_x$ causes initial increase of $i_p$, indicating no acceleration, but further increase of $i_x$ causes a decrease in $i_p$, and the minimum value, $i_{pb}$, then has a large positive error. In other instances, initial increase of $i_x$ causes initial decrease of $i_p$, indicating acceleration, but further increase of $i_x$ causes $i_p$ to decrease through zero so that $i_{pb}$ cannot be measured.

FACTORS INTERFERING WITH $i_{pb}$ MEASUREMENT

The unreliable performance of the circuit isolation device having isolation resistors of equal ohmic value and delivering current $i_x$ at constant rate of increase to each of two duplicated electrodes of equal area, was readily traced to the finding that the difference between the electrode potentials of the electrodes was significantly altered by increase in value of $i_x$.

The amount of change of this difference in electrode potential, and the polarity of the change, is now recognized to result from a number of factors, including the following inherent to a specific corrosion probe. Difference in area between the duplicated electrodes will cause the electrode with the slightly larger area to be slightly less polarized by a value of current $i_x$. When the ionic conductor has significant ohmic resistance, as with relatively dilute solutions, small difference in separation distance between the device anode and the two duplicated electrodes can introduce a significant difference of ionic conductor resistance in series with isolation resistors of equal ohmic value, and will cause that duplicated electrode with the greater separation distance to be less polarized.

In the presence of accelerated corrosion, additional factors related to the duration of the corrosion can erratically alter the difference in electrode potential between the duplicated electrodes as the current $i_x$ is increased. In accelerated corrosion, visible areas of localized anodic and cathodic action develop. The rate at which they develop, and the ratio of anodic/cathodic area developed, can vary between the duplicated electrodes according to an apparently random order. Since anodic area is more conductive than cathodic area, the development of the localized corrosion tends to produce unavoidable and erratic differences in cathodic polarizability between the duplicated electrodes with lapse of time, thereby causing change in difference between their electrode potentials as current $i_x$ is increased to each. Additionally, corrosion products tend to generally adhere to the anodic area, at least in part. The adherent corrosion products can operate to introduce additional ionic conductor resistance, and through variation is permeability, can alter the migration rate of cations as well as tending to increase the concentration of hydroxyl ions produced at the surface that is being polarized cathodically by current $i_x$.

Additional factors may be regarded to pertain to the environment in which the corrosion probe is operated. In the presence of ionic conductor flow rate, the two duplicated electrodes are usually positioned upstream from the anode electrode to avoid the turbulence which would result of the anode was positioned upstream. There are instances where the reverse positioning is favored, with the anode upstream. With either of these two alternative positionings, it is difficult to produce exactly the same flow rate on each of the two duplicated electrodes, and such difference, though slight, can cause difference in electrode polarizability particularly through its influence on the usual downstream distribution of the anodic area formed by the localized corrosion. Other differences can occur, as from slight temperature and concentration distribution differences.

In view of the operation of these many factors, the possibility of holding difference in electrode potential between the duplicated electrodes within the small limit required for precision measurement of the corrosion current $i_{pb}$, might be regarded as highly improbable. For example, the criteria might be proposed that the current $i_{pb}$ be measured within $\pm$ 10% precision. Then, when the corrosion current is measured with duplicated measured electrodes, the value of $e_{pa} + e_{pc}$ is generally taken as 0.020 volt. Change in difference of electrode potential between the two electrodes throughout the range of $i_x$ application would then have to be limited to $\pm(10\%)(0.020) = \pm 0.002$ volt. When the corrosion current is measured with a single measured electrode and a reference electrode duplicating the measured electrode, the value of $e_p$ is generally taken as 0.010 volt, and the change in difference of the electrode potential between the two electrodes would have to be limited to $\pm(10\%)(0.010) = 0.001$ volt. When the degree of accelerated corrosion is large, the maximum value of $i_x$ required to measure $i_{pb}$ as a true minimum value, in the sense that further increase of $i_x$ causes $i_p$ to then increase, is about five times larger than $i_A$, or maximum $i_x = 5i_A$. The possibility of maintaining such a small difference in electrode potential between the duplicated electrodes through such a comparatively large range of $i_x$ could easily be regarded as highly improbable.

DEVICE & METHOD

Experimental results made with corrosion cells which include variation in elemental electrode composition and in ionic conductor composition confirm the discovery that difference in the electrode potentials of duplicated electrodes can be held substantially constant during cathodic polarization by the circuit isolation device through circuitry to produce variation in the ohmic ratio of the two isolation resistors, and through method steps that include adjusting this ratio to maintain said difference in free electrode potential as the cathodic polarizing current is increased to near its full value, then removing said cathodic polarizing current, then allowing the free electrode potentials to return to their initial potential difference, and then performing the measuring steps of determining whether acceleration is present, and when present, measuring currents $i_{pb}$ and $i_x$. Device and method operate to produce substantially no data point scattering of the $i_{pb}$—time relationship to the extent illustrated in said U.S. Pat. No. 3,694,324 with pointwise measurement.

OBJECTS

The main object of this invention is an improved form of circuit isolation device and method of its operation, whereby the relationship between current $i_p$ from which corrosion current is measured, and cathodic current $i_x$ through which accelerated corrosion is detected aand measured, can be continuously measured with reliability and precision through the application of current $i_x$ at a selected rate of increase.

A further object is a form of circuit isolation device and method of operation that permit the manufacture and use of corrosion probes, including two duplicated electrodes and the anode electrode for passing current $i_x$, within easily attainable dimensional tolerances.

Additional objects following from the main object include measurement of $i_p$, $i_x$ relationship with minimum time lapse, the continuous recording of said relationship, simplification of automation requirements for measuring said relationship, and the ability to detect when a foreign material adheres to one of the duplicated electrodes to an extent interfering with the significance of the measurements.

THE FIGURES

OPERATION OF DEVICE & METHOD

Figure 3:
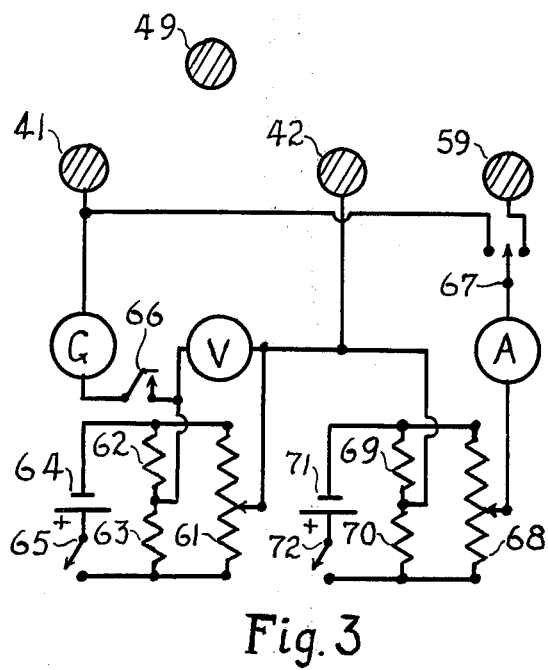
FIG. 3 is a basic circuit diagram of a device for measuring corrosion current with an electrode system including a measured, a reference, and an opposed electrode, and includes switching to measure corrosion current with an electrode system including two duplicated measured electrodes.
Figure 4:
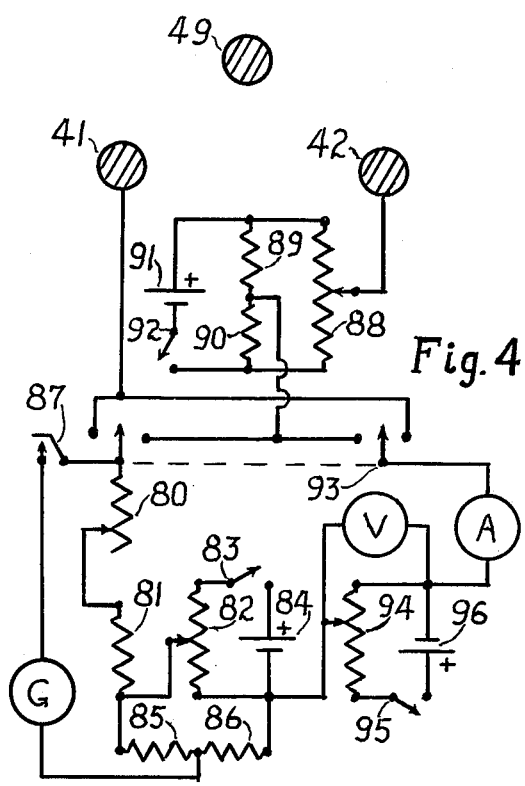
FIG. 4 is a basic circuit diagram of a device for measuring corrosion current with an electrode system including two duplicated measured electrodes, and a circuit making correction for voltage loss through the ionic conductor.

Duplicated electrodes 41 and 42 are shown in FIGS. 3 and 4.

FIG. 3 shows the basic circuit diagram of a device measuring the corrosion current of a single measured electrode 42, with electrode 41 operated as a reference electrode and with the addition of electrode 59 operated as the opposed electrode to pass measuring current to or from measured electrode 42. This device is also switchable to measuring the corrosion current of two duplicated measured electrodes, 41 and 42.

FIG. 4 shows the basic circuit diagram of an alternative form of device measuring the corrosion current of duplicated measured electrodes 41 and 42, and includes an alternative form of circuit for determining difference in free electrode potential between said electrodes, and additionally includes circuitry for correcting for the voltage loss caused by the ohmic resistance of the ionic conductor.

Figure 1:
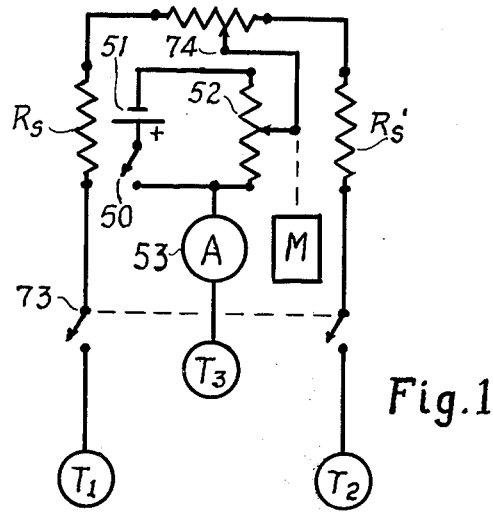
FIG. 1 is a circuit diagram of one form of the circuit isolation device of this invention.
Figure 2:
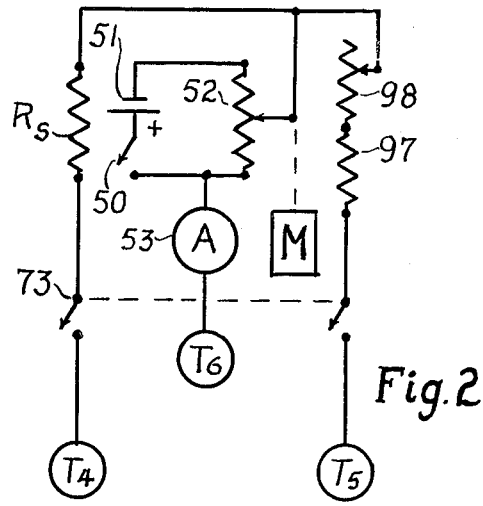
FIG. 2 is a circuit diagram of an alternative form of said circuit isolation device.

FIGS. 1 and 2 show alternative forms of the circuit isolation device of this invention, which can operate alternatively with the corrosion current measurement devices of FIGS. 3 and 4.

Method of operation of the device of FIG. 1 is first described through corrosion current measurements made with the device of FIG. 3. Electrodes 41, 42 and 49 are connected respectively to terminals $T_1$, $T_2$ and $T_3$ of FIG. 1. Measurement of the corrosion currents can be made at any time selected during progress of the corrosion. When the approximate value of corrosion current $i_A$ occurring at the free electrode potential of the measured electrode is not known from earlier measurement, it should be measured first for the purpose of selecting the proper ohmic range value for isolation resistor $R_s$.

In measuring corrosion current $i_A$, any difference between the free electrode potentials of duplicated electrodes 41 and 42 is first measured. The parallel connection of potentiometer 61 with the series connection of resistors 62 and 63, which are usually of equal ohmic value, is energized by battery 64 through the closing of switch 65. The arm of potentiometer 61 is then adjusted to that position where momentary closing of switch 66 shows no current through galvanometer G. The difference in free electrode potential, $\Delta E_f$, between electrodes 41 and 42 is then read on voltmeter V, regarded to have a zero-center scale from which voltage polarity is determined.

When current $i_A$ is measured by operating electrodes 41 and 42 as duplicated measured electrodes, the arm of switch 67 is turned to connect microammeter A to electrode 41. Meter A is also regarded to have a zero-center scale to read current flow in either direction. A value and polarity of applied DC voltage $e_p$, is selected within the range from slightly above zero to about 0.060 volt, and the arm of potentiometer 61 is adjusted to algebraically add this voltage to the difference in free electrode potential, $\Delta E_f$, as shown on voltmeter V. Since difference in free electrode potential can occur with either + or − polarity, and since voltage $e_p$ can be applied with either + or − polarity, possible combinations that may be encountered include $+\Delta E_f$ with $+e_p$, or $+\Delta E_f$ with $-e_p$, or $-\Delta E_f$ with $+e_p$, or $-\Delta E_f$ with $-e_p$. The inclusion of $\Delta E_f$ in measuring the DC voltage applied to the duplicated electrodes generally produces good precision with either $+e_p$ or $-e_p$ to the extent that a second measurement made with polarity reversal or $e_p$ is not justified, and instead the polarity of $e_p$ is reversed when another measurement is made after further time lapse in the progress of the corrosion.

The parallel connection of potentiometer 68 with the series connection of resistors 69 and 70, which are usually of equal ohmic value, is energized by battery 71 through the closing of switch 72. The arm of potentiometer 68 is adjusted to the position producing zero current through galvanometer G upon the momentary closing of switch 66, and this adjustment of the arm of potentiometer 68 is continued until the current measured at microammeter A initially undergoes a selected small rate of change, at which time measurement is made of corrosion current $i_p$. Then, $i_A = i_p(E_d/e_p)$. Switch 67 is then returned to its open-circuit position.

When the presence and extent of accelerated corrosion is not known for earlier measurement, the value of isolation resistors $R_s$ and $R_s'$ of FIG. 1 which are of equal ohmic value, is generally selected within a range capable of passing cathodic current $2i_x = 10i_A$. To minimize error in corrosion current measurement introduced by current flow through the isolation resistors from the voltage difference applied to the duplicated electrodes, the value of $R_s$ is generally selected from the largest ohmic range capable of delivering $2i_x$ with the driving force of the DC voltage represented by battery 51. In practice, this voltage can be as large as 60 volts, and $R_s$ can be as large as two megohms, depending on the qualities of lead wire and electrode insulations. The isolation resistors $R_s$ and $R_s'$ are connected by closing switch 73.

The circuit isolation device of FIG. 1 differs from that shown in my U.S. Pat. No. 3,694,324 by the addition of a ratio resistor here shown as potentiometer 74, with its resistor connecting between the isolation resistors $R_s$ and $R_s'$ and with its arm connecting to the negative lead from the source of variable DC voltage delivered from potentiometer 52. In effect, the position of the arm of potentiometer 74 varies the ohmic ratio between $R_s$ and $R_s'$, for the purpose of maintaining the value of $\Delta E_f$ during the increase of total cathodic polarizing current $2i_x$ from zero to its maximum required value. The ohmic value of potentiometer 74 must be large enough in proportion to the ohmic value of isolation resistor $R_s$, to maintain said potential difference $\Delta E_f$ within the wide range of corrosion interface composition and operation encountered with corrosion cells, and in practice the resistance of potentiometer 74 can be about 50% of that of isolation resistor $R_s$. This in effect produces an adjustable isolation resistor ratio ranging from $(100)/(100 + 50) = 0.67$, to $(100 + 50)/(100) = 1.50$.

FIG. 1 also introduces motor M to drive the arm of potentiometer 52 at a constant speed. The arm of potentiometer 52 can be driven across its resistor within a speed range from about 2 to more than 10 minutes, but in general practice the speed is generally selected within the range from about 5 to 10 minutes.

Measurement to determine the presence or absence of accelerated corrosion starts with the determination of $\Delta E_f$, which in the case of FIG. 3 is shown on voltmeter V. If corrosion current $i_A$ has just been measured, at time lapse of several minutes may be required for $\Delta E_f$ to return to its value existing before said corrosion current measurement.

The arm of potentiometer 74 is then positioned to hold the potential difference $\Delta E_f$ while current $2i_x$ is increased to generally at least 50% of its full value. The arm of potentiometer 52 is started at the position of zero voltage delivery. The arm of potentiometer 61 has already been positioned to produce no current through galvanometer G upon the momentary closing of switch 66. Switch 50 is closed to appply DC voltage 51 across potentiometer 52. Power is applied to motor M, and the arm of potentiometer 74 is adjusted toward that position where momentary closing of switch 66 continues to show no current through galvanometer G. This adjustment can generally be quickly arrived at while $2i_x$ is increased to about 30% of its full value, and verified while current $2i_x$ is increased further to about 50% of its full value.

Switch 50 is then opened, the arm of potentiometer 52 is returned to its position of zero voltage delivery, and power to motor M is disconnected.

A number of corrosion cells including variation in elemental electrode composition and wide variation in ionic conductor composition, concentration, and pH, have shown that it is usually possible to adjust the position of the arm of potentiometer 74 within the precision of holding the value of $\Delta E_f$ within about ±0.0006 volt, and this is regarded as a fortunate discovery.

To date, only one factor has been encountered that interferes with the adjustment of potentiometer 74. With electrodes in the form of rods mounted in glass tubing and sealed with beeswax, a crack in the wax seal at the glass-metal boundary and extending to the metal surface can prevent the adjustment of the arm of potentiometer 74 to a position where $\Delta E_f$ is maintained while $2i_x$ is increased. This finding has been accepted as a useful check on sealing quality.

Following this adjustment of the arm of potentiometer 74, electrodes 41 and 42 are allowed to return to substantially their initial voltage difference of $\Delta E_f$, as indicated from the deflection of galvanometer G decreasing to approach zero upon the momentary closing of switch 66 at small time intervals such as about 60 seconds. Upon removal of current $2i_x$, the extent that potential difference initially deviates from $\Delta E_f$, as well as the polarity of the deviation, is apparently related to retention properties of corrosion products adhering to the anodic area, and may also be affected by an adherent layer formed in some instances on the cathodic surface such as a carbonate scale when pH is above about 6. A total time lapse generally from 5 to 10 minutes is required for the potential difference to substantially return to $\Delta E_f$.

Measurement is next made of corrosion current $i_A'$, measured with the isolation resistors connected, which will have a value slightly greater than $i_A$, caused by the current, $i_s = e_p/(R_s + R_{74} + R_s')$.

Determination is them made of whether or not accelerated corrosion is present. While current $i_A'$ is undergoing only small rate of change, switch 50 is closed and power is applied to motor M. The arm of potentiometer 68 is adjusted with switch 66 closed, to maintain the current through galvanometer G at substantially zero. It is not uncommon for no adjustment of potentiometer 68 to be required for about the first minute of current $2i_x$ application, but thereafter potentiometer 68 will require adjustment in either the direction of increasing current or decreasing current through meter A.

When current $2i_x$ causes an increase in the value of $i_p$, to the extent of about 10%, the absence of accelerated corrosion is regarded to be confirmed, and all switches of the device are opened to allow the corrosion to continue undisturbed until the next measurement is made. The rate-determining corrosion current $i_R$, can be taken as $i_R = i_A'$, or if greater precision is required, as $i_R = i_A$.

When current $2i_x$ causes a decrease in the value of $i_p$, the measurement is continued to determine the minimum value, $i_{pb}$, and may also include determination of the value, $i_{xb} = 2i_x/2$, at which said minimum occurs. In general, $i_p$ decreases rapidly to a hold point, and through a small further increase in $2i_x$ the value of $i_p$ may remain substantially unchanged. Further increase in $2i_x$ then initiates increase in value of $i_p$, and the extension of measurement to include this increase is regarded to constitute insurance that the minimum value of $i_p$ has been measured. The value of $i_{pb}$ is taken as the minimum value, at the start of the hold region, and the value, $i_{xb} = 2i_x/2$ is similarly taken from a reading of microammeter 53. Current $i_{pb}$ is converted to bounding current $i_B$, as $i_B = i_{pb}(E_d/e_p)$, and with ionic conductors of low ohmic resistance, the rate determining corrosion current can be taken as, $i_R = 2.4(i_A') - i_B$.

In general, taking $i_R = i_{xb}$, introduces a positive error related to the speed at which motor M drives the arm of potentiometer 52, due to the lag between application of current $2i_x$ and the time required for the complete cathodic polarization producible by it to develop. However, such a positive error tends to oppose the negative error introduced by the presence of significant ionic conductor resistance.

Operation of the device of FIG. 3 with electrode 42 as the measured electrode, electrode 41 as the reference electrode, and electrode 59 as the opposed electrode, by connecting microammeter A to electrode 59 through switch 67, introduces additional manipulation complications. Difference between the free electrode potentials of electrodes 41 and 42, $\Delta E_f$, is measured as before. The adjustment of potentiometer 74 is also made in the same manner. However, the determination of current $i_{pb}$ must be measured from $i_p$ value as measured from polarization voltage of single polarity, either cathodic or anodic. The choice of which polarity to use becomes optional. Cathodic polarization produces a measured value of $i_A'$ in closer agreement with value of $i_A$ when it is measured from the average of cathodic and anodic measurements. Anodic polarization produces a slightly larger value of $i_A'$, which may contribute to correction for ionic conductor resistance. A serious difficulty is encountered in the adjustment of potentiometer 68 during application of the current $2i_x$. The adjustment of potentiometer 68 to hold the voltage between electrodes 41 and 42 constant is not in response to change in corrosion current alone. The cathodic polarization of electrode 42 by current $i_x$ introduces rapid and substantial change in potential difference between electrodes 42 and 59, which must be included in achieving continuous adjustment of potentiometer 68. Consequently, the need for a servo null drive from the voltage across galvanometer G to the arm of potentiometer 68 approaches the importance of practical necessity.

Ionic conductor resistance, when significant and not corrected for, not only introduces substantial negative error in corrosion current measurement but also diminishes the sensitivity with which difference in free electrode potential $\Delta E_f$, between duplicated electrodes 41 and 42, can be measured. The circuit of FIG. 3, when operated with duplicated measured electrodes 41 and 42, produces satisfactory accuracy in ratedetermining current $i_R$ measurement when ionic conductor resistance is negligible. The circuit of FIG. 3, when operated with electrode 42 as the measured electrode and electrode 41 as the reference electrode, produces satisfactory accuracy when ionic conductor resistance does not exceed a relatively small value, but the reference electrode cannot be positioned to eliminate error with high ionic conductor resistance which may range up to about 75,000 ohms between duplicated electrodes 41 and 42. The circuit of FIG. 4 includes means for correcting for ionic conductor resistance through the addition of compensating voltage, and this compensating voltage maintains the precision of $\Delta E_f$ determination in the presence of high ionic conductor resistance. FIG. 4 also illustrates the use of a circuit for the specific purpose of equalizing the difference in free electrode potential between duplicated electrodes.

Operation of the basic circuit of FIG. 4 starts with the adjustment of rheostat 80. The ohmic value of this resistor is adjusted to equal the measured ohmic value of ionic conductor resistance occurring between electrodes 41 and 42 at the time of measurement. It may further include the ohmic value of lead wires from the measurement device to the corrosion cell when they are separated by a significant distance. It may additionally include the ohmic resistance of the potential equalizing circuit when adjusted to oppose difference in free electrode potential between electrodes 41 and 42. Resistance 81 is made equal to the ohmic resistance of microammeter A, taking into account the current range at which the meter is operated in measuring current $i_A'$. The sum of the ohmic value of resistors 80 and 81 is then equal to the total ohmic resistance that should be corrected for when a measured DC voltage is applied to the duplicated electrodes in corrosion current measurement.

The source of voltage for correcting for IR loss is delivered from potentiometer 82 after it is energized by the closing of switch 83 in series with battery 84. The voltage delivered from potentiometer 82 is applied across duplicated resistors 85 and 86, according to my U.S. Pat. No. 3,607,673. Galvanometer G is connected across the series connection of resistors 80, 81 and 85 through momentary-close switch 87. The arm of potentiometer 82 is adjusted to maintain zero current through the galvanometer during all measurements. While this can be accomplished by manual adjustment, it is more efficiently and easily handled by a null servo drive system between galvanometer G and the arm of potentiometer 82 with switch 87 closed. Then, for any current through microammeter A, either in corrosion current measurement or in the determination of $\Delta E_f$, the voltage added through resistor 85 equals the voltage loss through resistors 80 and 81. The voltage across duplicated resistor 86 then adds voltage correction for the circuit resistances represented by resistors 80 and 81.

The circuit for opposing any difference in free electrode potential $\Delta E_f$ between the duplicated electrodes 41 and 42 at the time of measuring corrosion currents $i_A$ and $i_A'$ includes potentiometer 88 in parallel with the series connection of resistors 89 and 90, which are usually of equal ohmic value, activated by battery 91 upon the closing of switch 92. The difference in the free electrode potentials, $\Delta E_f$, is determined, in that it is opposed with precision by the adjustment of the arm of potentiometer 88, but its measurement in voltage units is not required. Switch 93, determining the polarity of the DC voltage applied in the corrosion current measurement, is turned in a direction to connect electrodes 41 and 42. Usual practice includes the reversal of this polarity after each measurement made during progress of the corrosion. Microammeter A is thereby connected in series with the duplicated electrodes through potentiometer 94, which is of relatively low ohmic resistance. Potentiometer 88 is adjusted for zero current through microammeter A. This adjustment can be made within ±0.2 microampere on a 100 microampere meter of 3,000 ohms internal resistance, from which it is calculated that $\Delta E_f$ is determined within a precision of $e = iR = \pm(2\times10^{-7})(3\times10^3) = \pm0.0006$ volt.

Corrosion current is then measured by activating potentiometer 94 by the closing of switch 95 to connect battery 96. Potentiometer 94 is adjusted to deliver DC voltage to the duplicated measured electrodes within the range described above as measured on voltmeter V, and measurement is made when the current shown by microammeter A initially approaches selected slow rate of change.

Referring to the circuit isolation device of FIG. 2, the ohmic value of isolation resistor $R_s$ is selected after measurement of corrosion current $i_A$ occurring at the free electrode potential, as described above in connection with FIGS. 1 and 3. The circuit isolation device of FIG. 2 differs from that of FIG. 1 through the replacement of ratio resistor or potentiometer 74 and resistor $R_s'$ of FIG. 1 with resistor 97 and ratio resistor or rheostat 98. The isolation resistor ratio range of FIG. 1 can be applied to FIG. 2. The value of resistor 97 is $(100/150)R_s = 0.67R_s$. The value of rheostat 98 is expressed through the equation, $0.67(R_s) + R_{98} = 1.50R_s$, from which $R_{98} = 0.83R_s$.

In detecting the presence or absence of accelerated corrosion, and the measurement of currents $i_{pb}$ and $i_{xb}$ when acceleration is present, terminals $T_4$, $T_5$ and $T_6$ of FIG. 2 are connected to electrodes 41, 42 and 49 of FIG. 4. Rheostat 98 is adjusted in the manner described for potentiometer 74 of FIG. 1. Corrosion current $i_A'$ is measured with FIG. 4. The measurement of currents $i_{pb}$ and $i_{xb}$ follow the equivalent steps described for FIGS. 1 and 3.

For the purpose of maintaining potential difference $\Delta E_f$ initially existing between duplicated electrodes during subsequent cathodic polarization of the electrodes by currents $i_x + i_x' = 2i_x$, the circuits of FIGS. 1 and 2 can be considered as entirely equivalent. However, potentiometer 74 of FIG. 1 is smaller than rheostat 98 of FIG. 2 for the same ratio range in each figure by the percentage, $(100)(50/83) = 60\%$ of that of rheostat 98. When the ohmic values required for potentiometer 74 and rheostat 98 are determined by large ohmic value selected for isolation resistor $R_s'$, the electromechanical ruggedness of potentiometer 74 can be more easily met.

In general, the corrosion mechanism and rate of an electronic conductor corroded by an ionic conductor under attending conditions of environment is measured with best precision and accuracy through corrosion current measurement made with FIG. 4, which includes correction for ionic conductor resistance, and with FIG. 1 using potentiometer adjustment of isolation resistor ratio. The voltage $\Delta E_d$, which can alternatively be noted from the position of the arm of potentiometer 88, or be measured, indicates difference in the accelerated corrosion occurring to the duplicated electrodes, and after the corrosion has approached a steady rate, this voltage tends to become small. Corrosion current can be converted in the measurement device to, $i_{corr.} = i_p(E_d/e_p)$, and can be recorded from the voltage drop across microammeter A or alternatively from the voltage drop across resistance 81, using a potentiometric recorder with high input resistance and zero offset voltage, and having a time drive abscissa axis. When $i_{xb}$ is to be included in the recording, an X-Y recorder is used. In the measurement of corrosion current $i_A'$, the abscissa input is taken from a source of voltage increasing at a constant rate, and its response is calibrated to a selected time scale. Then, in measuring $i_{pb}$ and $i_{xb}$, the abscissa input is taken from microammeter A of FIGS. 1 or 2, and its response is calibrated to a microampere scale for $2i_x/2$. With proper care in making up the corrosion cell, the corrosion performances of the duplicated electrodes generally differs by only a small amount, which, if of interest, can be measured from initial and final weighings of the electrodes.

The recording of data obtained through the operation of the circuit isolation device of this invention is found to follow characteristic forms in the measurement of unaccelerated and accelerated corrosion, and these forms are found to be independent of electronic-ionic conductor interface composition and environment factors such as temperature and flow rate. The purpose of the examples which follow is therefore to illustrate these general forms of recorded measurements.

EXAMPLE 1

Adjustment of Isolation Resistor Ratio

Figure 5:
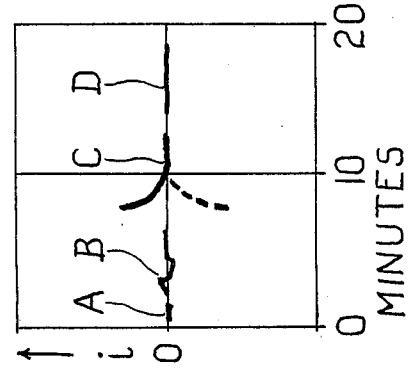
FIG. 5 illustrates recordings made in the adjustment of isolation resistor ratio.

Characteristic forms of measurements recorded in the adjustment of isolation resistor ratio are shown in FIG. 5. Abscissa is shown in units of 10 minutes per inch chart speed, which can be varied according to specific requirements. In general a speed of 20 minutes per inch is satisfactory. Ordinate is shown as corrosion current, with zero as the current at which $\Delta E_f$ is determined. Specific units of current are not shown because the recordings appear independent of unit size ranging from 2 to 200 microamperes per inch.

In starting measurements, at a time selected during progress of the corrosion, the value $\Delta E_f$ is first determined, and the recording pen is set at zero current. To insure that the potential of the measured electrode, whether in the form of a single electrode 42 or of duplicated electrodes 41 and 42, is free from previous polarization, a recording can be made during a short period such as two minutes, as is shown by line A of FIG. 5, which shows the holding of zero current.

Recording can be made during adjustment of the isolation resistor ratio to hold $\Delta E_f$ at the zero current position during application of cathodic polarizing current $2i_x$. This is shown in line B of FIG. 5, and it is to be understood that the amount of waviness of this line relates to the degree of refinement used in making this adjustment.

After measuring corrosion currents $i_A'$, $i_{pb}$, and sometimes $i_{xb}$, the electrodes require several minutes to return to their original free electrode potentials. Line C of FIG. 5 shows such recovery, which may occur either in the form of current decreasing to zero, or negative current increasing to zero, as shown by the dotted portion of the line.

When desired, the setting of the isolation resistor ratio can be checked by first allowing the electrodes to return to their free electrode potentials as shown in line C, and by then recording the effect of again applying current $2i_x$. As shown in line D of FIG. 5, a substantially horizontal straight line can be obtained.

When the corrosion cell is operated with fixed factors of environment such as temperature and flow rate, the position at which the arm of potentiometer 74 is set does not vary much between alternate measurements when the polarity of the DC voltage applied in measuring the corrosion current is reversed after each measurement. A sudden large variation in the required position of the arm of potentiometer 74 is found to be caused by the adhesion of foreign material to one electrode, such as algae or "glop", and can be taken as a warning that the corrosion rate measurements are being interfered with.

EXAMPLE 2

Determination of Unaccelerated Corrosion

Figure 6:
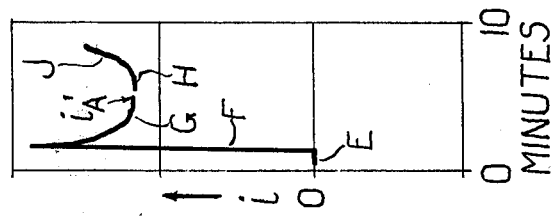
FIG. 6 illustrates recordings made in determining the absence of accelerated corrosion.

The measurement of corrosion current $i_A'$ and the determination of unaccelerated corrosion mechanism are illustrated in FIG. 6. An initial recording of short duration, E, is generally made to prove the zero current setting with the recorder. To avoid a large initial polarizing current upon applying the polarizing voltage $e_p$, this voltage can be delivered from a motor driven potentiometer to apply the voltage from zero to $e_p$ within a selected time such as about one minute, and this is shown in line F of the recording. Immediately thereafter, the current generally decreases to a selected slow rate of change shown by curve G, from which current $i_A'$ is measured. Current $2i_x$ is then applied at a selected rate of increase. A small time interval during which the recording pen is lifted, can be used to indicate when said current is applied. The recorded curve generally has a small duration H, of no current change, after which the current increases rapidly along line J. Recording is generally continued until this current increase amounts to about 10% of current $i_A'$, but in automation, the detection of this increase can be reduced to a smaller percentage. The current increase determines that the corrosion is occurring through unaccelerated mechanism.

EXAMPLE 3

Measurement of $i_A'$ and $i_B$

Figure 7:
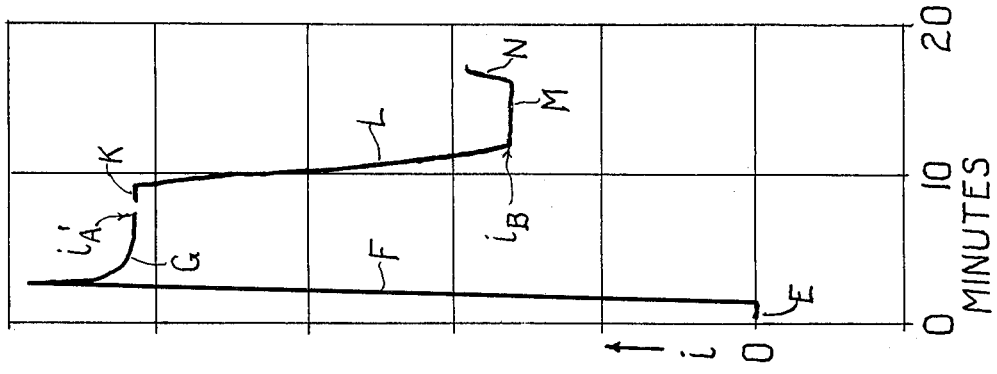
FIG. 7 illustrates recordings made in measuring the currents of accelerated corrosion against a time axis.

Measurement of the corrosion current $i_A'$ remains the same in form when the corrosion is undergoing acceleration, and includes recorded portions E, F and G as shown in FIG. 7. Measurement of bounding current $i_B$ can be made by continued recording along a time abscissa, as shown in this figure. In general there is an initial portion K of substantially no change in current. In the presence of acceleration, this is followed by a region of rapid current decrease, L, that is terminated by a second line of substantially no change in current, M. Bounding current $i_B = (i_{pb})(E_d/e_p)$, is measured at the intersection point of portions L and M, and it is to be understood that the measured value of $i_B$ in proportion to the value of $i_A'$ is determined by the intensity of the acceleration through which the corrosion is occurring. The recording can include a line of increasing current N, following hold line M, to confirm that $i_B$ is measured as the minimum value of corrosion current.

EXAMPLE 4

Additional Measurement of $i_{xb}$

Figure 8:
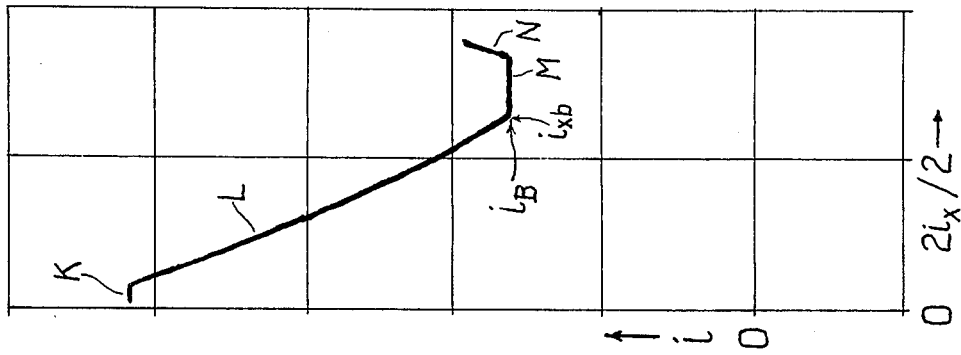
FIG. 8 illustrates recordings made in measuring the currents of accelerated corrosion against an axis calibrated in units of cathodic polarizing current.

When $i_{xb}$ is to be measured, an X-Y recorder is used. During the measurement of corrosion current $i_A'$, the abscissa is operated as a time drive through the application of an input voltage increasing at a selected rate. During the measurement of currents $i_B$ and $i_{xb}$, as shown in FIG. 8, the abscissa is calibrated and operated to measure current $2i_x$, or alternatively $2i_x/2$, from which current $i_{xb}$ can be read directly. The form of the recording contains the same regions, K, L, M and N. The value of $i_{xb}$ is taken at the intersection of the L and M lines.

Glossary of Symbols & Terms

| Symbol | Definition | Method of Determination |
|---|---|---|
| SINGLE MEASURED ELECTRODE: | | |
| $E_f$ | Free electrode potential, the undisturbed electrode potential at naturally occuring corrosion rate. | Measured |
| $\Delta E_f$ | Difference between free electrode potentials of two electrodes | Measured |
| $i_p$ | Polarizing current, passed through interface of measured electrode during polarization voltage measurement | Measured |
| $e_{pc}$ | Polarization voltage when $i_p$ is cathodic | Measured |
| $e_{pa}$ | Polarization voltage when $i_p$ is anodic | Measured |
| $e_p$ | Polarization voltage selected in calculating corrosion current | See calculation of $i_A$ |
| $E_d$ | Direct Voltage of the Interface Electrode System when $e_p = e_{pc} + e_{pa}$ | Measured in U.S. Pat. No. 3,156,631. With unaccelerated corrosion, where $i_A = i_R$. The Interface Electrode System shows that when $i_p$ is taken as $i_p = i_A$, then $e_{pa} + e_{pc} = 0.028$ volt, the Direct Voltage $E_d$. In applying $E_d$ to $i_A$ measurement in general, when $e_{pa} + e_{pc}$ is selected within the range 0.03 to 0.06 v., $E_d$ is taken as 0.028 volt; when $e_{pa} + e_{pc}$ is selected within the range 0.001 to 0.03 v., $E_d$ is taken as 0.030 volt. |
| $i_A$ | Corrosion current at potential $E_f$ | When $e_p = e_{pc} + e_{pa}$, $i_A + i_p(E_d/e_p)$; When $e_p = e_{pc}$, or $e_p = e_{pa}$, or $e_p = (e_{pc} + e_{pa})/2$, $i_A = i_p (\frac{1}{2}E_d/e_p)$ |
| TWO DUPLICATED ELECTRODES: | | |
| $e_p$ | DC voltage applied to duplicated electrodes to measure corrosion current | Measured When ionic conductor resistance is negligible, or is corrected for by added applied DC voltage, $e_p = e_{pc} + e_{pa}$ |
| $i_A$ | Corrosion current at potential $E_f$ | $i_A = i_p(E_d/e_p)$ |

-continued
Glossary of Symbols & Terms

| Symbol | Definition | Method of Determination |
|---|---|---|
| ACCELERATED CORROSION: | | |
| $i_A''$ | Corrosion current $i_A$ when measured with isolated resistors connected | Measured in terms of its $i_p$ and $e_p$ values. Calculated, as with $i_A$ |
| $i_s$ | Isolation resistor current passed through the isolation resistors by the DC voltage across the duplicated electrodes during corrosion current measurement | $i_s = i_A' - i_A$ |
| $2i_r$ | Total cathodic polarizing current passed to duplicated electrodes by circuit isolation device | Measured |
| $i_{rs}$ | Current passed to electrode connected to $R_s$ | Could be measured |
| $i_{rs}'$ | Current passed to electrode connected to $R_s'$ | Could be measured |
| $i_r$ | Cathodic polarizing current passed to measured corrosion interface | For practical purposes, $i_{rs} = 2i_r/2$ |
| $i_{pb}$ | Minimum value of $i_p$ produced by $i_r$ when acceleration is present | Measured |
| $i_B$ | Bounding current of unaccelerated corrosion | Calculated, as with $i_A$, using $i_{pb}$ value |
| $i_{rb}$ | Value of $i_r$ at which $i_{pb}$ is first produced | Measured as $i_{rb} = 2i_{rb}/2$ |
| $i_R$ | Rate-determining corrosion current | In absence of acceleration: $i_R = i_A = i_B$ In presence of acceleration: $i_R = 2.4(i_A) - i_B$ |

I claim:

1. A circuit isolation device having variable isolation resistor ratio, for cathodically polarizing two duplicated electrodes positioned in the non-gaseous ionic conductor of a corrosion cell without interfering with corrosion current measurement made on one or both of said electrodes, including two isolation resistors, two cathodic terminals each connected to a first end of said isolation resistors and for connection to said two electrodes, a source of DC voltage, means for variable voltage delivery connected across said source of DC voltage, a DC current indicating device connected in series with a lead from said means for variable voltage delivery, an anode terminal connected to the positive lead from said means for variable voltage delivery and for connection to an anode electrode, a ratio resistor connected in series with a second end of said two isolation resistors, and a connection from the negative lead of said means for variable voltage delivery to a contact arm traversable along the resistor element of said ratio resistor.

2. The device of claim 1, in which said two isolation resistors are of substantially equal ohmic value and in which said ratio resistor comprises a potentiometer.

3. The device of claim 1, in which one of said isolation resistors is of smaller ohmic value, and in which said ratio resistor comprises a rheostat with its resistive terminal connected to said second end of said smaller ohmic value isolation resistor.

4. The device of claim 3, wherein said connection from the negative lead of said means for variable voltage delivery is to said contact arm of said rheostat.

5. The device of claim 1, in which said ratio resistor is of ohmic value proportioned with respect to the ohmic values of said isolation resistors to in effect produce isolation resistor ratio adjustable within the range from about 0.67 to 1.5.

6. The device of claim 1, including means to increase the voltage delivered from said means for variable voltage delivery at a substantially constant rate of voltage increase from zero to maximum within a time lapse range selectable from about 3 to 10 minutes by a source of motive power.

7. The device of claim 1, in which said two isolation resistors and said ratio resistor are selectable through switching as a series of graduated ohmic ranges.

8. The method of operating a circuit isolation device having variable isolation resistor ratio for continuous measurement of the effect of cathodic polarization on measured corrosion current, including the steps of connecting duplicated electrodes to a corrosion current measuring device having circuitry for determining difference in voltage difference $\Delta E_f$ between the free electrode potentials of said duplicated electrodes, measuring on at least one of said duplicated electrodes the corrosion current $i_A$ occurring at free electrode potential, connecting said electrodes to the cathode terminals of a circuit isolation device having variable isolation resistor ratio, connecting the anode terminal of said device to an anode electrode spaced substantially equidistant from said duplicated electrodes, selecting an ohmic range value of isolation resistors and ratio resistor to pass total cathodic polarizing current $2i_x$ to said electrodes of value equal to about ten times said measured current $i_A$, and to limit the current passed through said isolation resistors by the DC voltage difference between the duplicated electrodes during subsequent corrosion current measurement to about fifteen percent of the value of said current $i_A$, selecting a rate of voltage increase at which the source of variable voltage of said circuit isolation device is to be operated, allowing the electrode potentials of said duplicated electrodes to return to said voltage difference of $\Delta E_f$ after said current $i_A$ measurement, delivering said selected rate of voltage increase starting at zero voltage while adjusting the ratio resistor of said circuit isolation device to maintain said voltage difference $\Delta E_f$ through increase of said current $2i_x$ to a value of about 5 times that of said current $i_A$, reducing said delivered voltage to zero and disconnecting the voltage drive of said device, allowing the voltage difference between said duplicated electrodes to return to said voltage difference $\Delta E_f$, measuring the corrosion current $i_A'$ occurring at free electrode potential when the isolation resistors are connected to said duplicated electrodes, then, while continuing corrosion current measurement, delivering said selected rate of voltage increase while measuring the relationship between corrosion current and the cathodic polarizing current $2i_x$, and when the measured corrosion current increases above $i_A'$ or increases above a minimum value, $i_B$, disconnecting said duplicated electrodes from the corrosion current measurement device and from the circuit isolation device, whereby the relationship between corrosion current and cathodic polarizing current $2i_x$ can be continuously recorded to detect the presence of accelerated corrosion mechanism and to measure accelerated corrosion rate.

9. The method of claim 8, in which corrosion current is measured on said duplicated electrodes.

10. The method of claim 8, in which corrosion current is measured on one of said duplicated electrodes, the other duplicated electrode being operated as a reference electrode, and an additional electrode is introduced and operated as the opposed electrode for passing current in the corrosion current measurements.

11. The method of claim 8, in which the measurement of corrosion current $i_A$ for selecting ohmic range of isolation resistors and ratio resistor, is avoided by using the value of current estimated from the trend of preceding measurements of current $i_A'$.

* * * * *